United States Patent
Strölin

(10) Patent No.: US 11,512,837 B2
(45) Date of Patent: Nov. 29, 2022

(54) LAMP HOUSING AND OPERATING LAMP HAVING A LAMP HOUSING

(71) Applicant: Karl Leibinger Medizintechnik GmbH & Co. KG, Mühlheim (DE)

(72) Inventor: Joachim Strölin, Rietheim (DE)

(73) Assignee: Karl Leibinger Medizintechnik GmbH & Co. KG, Mühlheim (DE)

( * ) Notice: Subject to any disclaimer, the term of this patent is extended or adjusted under 35 U.S.C. 154(b) by 0 days.

(21) Appl. No.: 17/290,921

(22) PCT Filed: Nov. 8, 2019

(86) PCT No.: PCT/EP2019/080727
§ 371 (c)(1),
(2) Date: May 3, 2021

(87) PCT Pub. No.: WO2020/094857
PCT Pub. Date: May 14, 2020

(65) Prior Publication Data
US 2021/0388969 A1  Dec. 16, 2021

(30) Foreign Application Priority Data
Nov. 8, 2018  (DE) .......................... 202018106344.8

(51) Int. Cl.
*F21V 15/01*    (2006.01)
*F21V 31/00*    (2006.01)
(Continued)

(52) U.S. Cl.
CPC ............ *F21V 15/01* (2013.01); *F21V 31/005* (2013.01); *A61B 90/35* (2016.02); *F21W 2131/205* (2013.01)

(58) Field of Classification Search
CPC ....... F21V 15/01; F21V 31/005; A61B 90/35; F21W 2131/205
See application file for complete search history.

(56) References Cited

U.S. PATENT DOCUMENTS

| 4,037,096 A | 7/1977 | Brendgord et al. |
| 8,292,804 B2 * | 10/2012 | Marka ..................... A61B 90/35 600/249 |

(Continued)

FOREIGN PATENT DOCUMENTS

| GB | 739621 | 11/1955 |
| JP | 2004288474 | 10/2004 |
| WO | 2012/156617 | 11/2012 |

OTHER PUBLICATIONS

International Search Report dated Dec. 11, 2019 from International Application No. PCT/EP2019/080727.

*Primary Examiner* — Tsion Tumebo
(74) *Attorney, Agent, or Firm* — Beyer Law Group LLP

(57) ABSTRACT

The invention relates to a lamp housing (1) for an operating lamp (2), in which lamp housing at least one illuminant (3) can be installed, said lamp housing comprising: a housing body (4); a closure element (5), which closes the housing body (4); and a bearing device (6) for fastening the lamp housing (1) to a supporting device (7). The lamp housing (1) has a support (8) formed separately from the housing body (4), by means of which support a force introduced via the closure element (5) and/or a weight force of the lamp housing (1) can be transferred to the bearing device (6). The invention further relates to an operating lamp (2) having a lamp housing (1), in which lamp housing an illuminant (3) is installed in a dust-tight manner.

14 Claims, 3 Drawing Sheets

(51) Int. Cl.
*A61B 90/35* (2016.01)
*F21W 131/205* (2006.01)

(56) References Cited

U.S. PATENT DOCUMENTS

| | | | |
|---|---|---|---|
| 11,153,953 B2* | 10/2021 | Alexanderson | F21V 23/0471 |
| 11,156,339 B2* | 10/2021 | Dahlen | F21V 15/01 |
| 2013/0027935 A1* | 1/2013 | Ladewig | F21V 29/508 |
| | | | 29/592.1 |
| 2013/0088861 A1* | 4/2013 | Wu | F21V 21/00 |
| | | | 362/244 |
| 2014/0268751 A1 | 9/2014 | Boccoleri et al. | |
| 2014/0340907 A1* | 11/2014 | Yu | F21K 9/20 |
| | | | 362/294 |
| 2017/0016601 A1* | 1/2017 | Pouladian | F21S 8/033 |
| 2017/0030570 A1* | 2/2017 | Yang | F21V 29/763 |
| 2018/0100641 A1* | 4/2018 | Verfuerth | F21V 29/70 |
| 2018/0220508 A1* | 8/2018 | Pilat | F21S 8/061 |

* cited by examiner

LAMP HOUSING AND OPERATING LAMP HAVING A LAMP HOUSING

The invention relates to a multi-part lamp housing for a medical operating lamp, in which lamp housing at least one illuminant can be installed. The lamp housing comprises a housing body, a closure element which closes the housing body, and a bearing device for fastening the lamp housing to a supporting device such as a supporting arm. The invention further relates to an operating lamp comprising a lamp housing, with an illuminant being installed in the lamp housing and the lamp housing sealing the illuminant against the environment in a dust-tight manner.

From prior art, lamp housings for operating lamps are known already. For example, DE 10 2011 102 638 A1 or DE 10 2011 102 645 A1 shows a multi-part operating lamp. In those operating lamps, frequently an upper part is connected to a lower part through lateral screws.

It is the drawback of the prior art, however, that the operating lamps have a dead weight of up to 10 kg, and additionally forces for moving the operating lamp must be transmitted via the lamp housing to the supporting device. The stability of the previously known lamp housings is not sufficiently high to absorb the high forces.

Hence, it is the object of the invention to avoid or at least minimize the drawbacks of the prior art. In particular, a lamp housing for a medical operating lamp is intended to be provided which is especially stable, safe and long-lasting. In addition, the design of the lamp housing is intended to be as simple and as easy to sterilize as possible so as to allow for use in the operating room.

The object of the invention is achieved, in accordance with the invention, for a generic device by the lamp housing having a support formed separately from the housing body by means of which support a force introduced via the closure element, in particular for moving the lamp housing and, resp., the operating lamp, and/or a weight force of the lamp housing can be transferred to the bearing device. Consequently, this means that the major part of the forces is not transferred by the housing body but solely via the supporting structure formed by the support from the force introduction point, such as a central handle, to the bearing device and then to the supporting device.

This offers the advantage that an especially stable lamp housing can be provided. The use of the additional support in the lamp housing, by which the forces to be absorbed are transferred, enables an especially safe and long-lasting lamp housing to be provided, as the housing body is hardly loaded. Thus, safe operation can be ensured, even if parts of the lamp housing such as the housing body are damaged.

Advantageous embodiments are claimed in the subclaims and shall be explained in detail below.

According to a preferred embodiment, the support and the housing body can be made from different materials. Preferably, the material of the support has a higher strength and/or rigidity than the material of the housing body. As the forces to be transferred are absorbed by the support serving as a supporting structure, the housing body need not have high strength and stability. By reducing the forces acting on the housing body, the requirements to the material of the housing can be reduced.

It is especially preferred when the support is made from steel. In this way, the forces can be easily absorbed and transferred by the structure. A steel cross-beam is an especially preferred embodiment for the support because of its simple structure and its strength.

In an advantageous development, the closure element can be fastened, preferably directly, to the support via a connecting element such as screws. Alternatively, or additionally, the closure element can be arranged on the housing body. Due to the fastening of the closure element to the housing body, advantageously the flux of force is not guided via the housing body but directly to the bearing device of the lamp housing.

Preferably, the bearing device is directly fastened to the support. For example, the bearing device may be formed by a one-sided lateral bearing.

In accordance with a preferred development, the lamp housing may include gripping device and/or a covering device, the gripping device and/or the covering device being adapted to be fastened, preferably exchangeably, to the closure element while covering the connection element. Therefore, this means that the lamp housing has no external visible connection elements. This allows the lamp housing to be easily wiped off and kept sterile. Since the connection element must transfer sufficiently high forces, it is of advantage when it is formed by plural, such as four, screws which connect the closure element to the support and/or the housing body. Thus, the lamp housing can be easily closed via the connection element, as only the connection element is required on the closure element. The interior of the lamp housing is thus easily accessible for service, and the closure element is fastened in an especially efficient manner.

Since the connection element, which is usually made from metal, is additionally covered, such as by a handle or any other cover, the sterilizability can be improved by selecting a suitable handle or a suitable cover. A handle or a cover made from plastic is especially advantageous. In addition, the handle or, resp., the cover is preferred to be also arranged to the closure element via a connecting device which can especially be easily wiped off and, resp., sterilized. For example, one or more tommy screws have turned out to be a suitable connecting device. It has turned out to be advantageous, even independently of providing the support, to provide covered connection elements.

In an advantageous embodiment, the housing body can include an upper part and a lower part formed separately from the upper part and being connected to the upper part, wherein the lower part is formed to be light-transparent at least in the region of an optical path produced by the illuminant. Thus, the housing body can be easily opened to replace the illuminant.

It is additionally of advantage when the closure element fastens the lower part, preferably in a prestressed manner, to the upper part. Thus, the lamp housing can be easily closed via the closure element and, consequently, easily via the connection element. For closing the lamp housing, it is therefore only necessary to attach the connection element, i.e., to screw in the screws. Hence, the interior of the lamp housing is easily accessible for service and the closure element is fastened in an especially efficient manner. Thus, the upper part only has to absorb the closing force by which the lower part is fastened to the upper part. Therefore, hardly any forces are acting on the upper part.

As an advantageous embodiment, the upper part may be made from polyurethane and/or the lower part may be made from tempered glass such as mineral glass. These materials have proven to be especially suitable. The lower part is preferably designed to be substantially flat.

In addition, it is of advantage when the housing body, especially the upper part, is arranged on the support. The upper part is preferably directly screwed to the support.

According to a preferred development, the closure element may be a holding ring disposed centrally on the lamp housing. The force is thus introduced centrally through the closure element and is transmitted via the support to the lateral bearing. Preferably, the closure element is arranged substantially axially in parallel to the optical path of the illuminant so that the closure element does not impair the luminosity of the illuminant. The closure element may be made from plastic, for example.

It is further useful when the closure element includes an annular portion passing through a recess of the lower part and a preferably peripheral flange portion which projects radially outwardly from the annular portion and abuts on an outer face of the lower part. The prestressing force can be applied via the flange portion to the lower part in the direction of the upper part. Preferably, the connection element is arranged close to the flange portion so that forces can be appropriately transferred. A suitable option for connecting the gripping device such as the handle can be formed by providing the annular portion. Preferably, an end of the annular portion facing away from the flange portion abuts (in the mounted state) on an inner face of the upper part. Hence the prestress can be applied. In addition, this helps increase the stability.

The lamp housing is especially preferred to include, for sealing an interior of the lamp housing, a housing body seal interposed between the upper part and the lower part, and/or a closure seal interposed between the lower part and the closure element, especially the flange portion. Thus, dust or any other impurities can be safely prevented from penetrating the interior of the lamp housing between the plural components of the lamp housing.

The object of the invention is also achieved by an operating lamp comprising such lamp housing, with an illuminant being installed in the lamp housing and the lamp housing sealing the illuminant against the environment in a dust-tight manner.

In other words, the invention relates to a multi-part medical operating lamp, wherein a closure unit in the form of a holding ring, for example, is installed (in the operating lamp) while closing the operating lamp. In prior art, screw connections are visible in operating lamps. The invention relates to an operating lamp/a lamp housing having a one-sided bearing. It is stable, IP-tight (sealed) and has no visible screw connection. The lamp housing is closed by means of the closure glass. The lamp includes a central handle. A central holding ring is located behind said removable handle. The closure glass is screwed by said holding ring. The closure glass is a hardened mineral glass adapted to absorb very high forces. The central screw connection on the one hand holds the glass itself and pulls it onto the bearing surface at the outer diameter of the housing. Both the central fastening ring and the bearing surface on the outside include seals. This way of closing the lamp is very simple. Merely four screws are required on the holding ring. Both the central holding ring and the screws are covered by the central handle. The force is introduced via the lateral bearing by means of a steel beam (cross-beam) to the central holding ring. The housing itself is made from PUR (polyurethane) and absorbs only low forces.

In the following, the invention will be illustrated by means of Figures, wherein.

The drawings are merely schematic and serve for the comprehension of the invention. Like elements are marked by like reference numerals.

Figure 1:
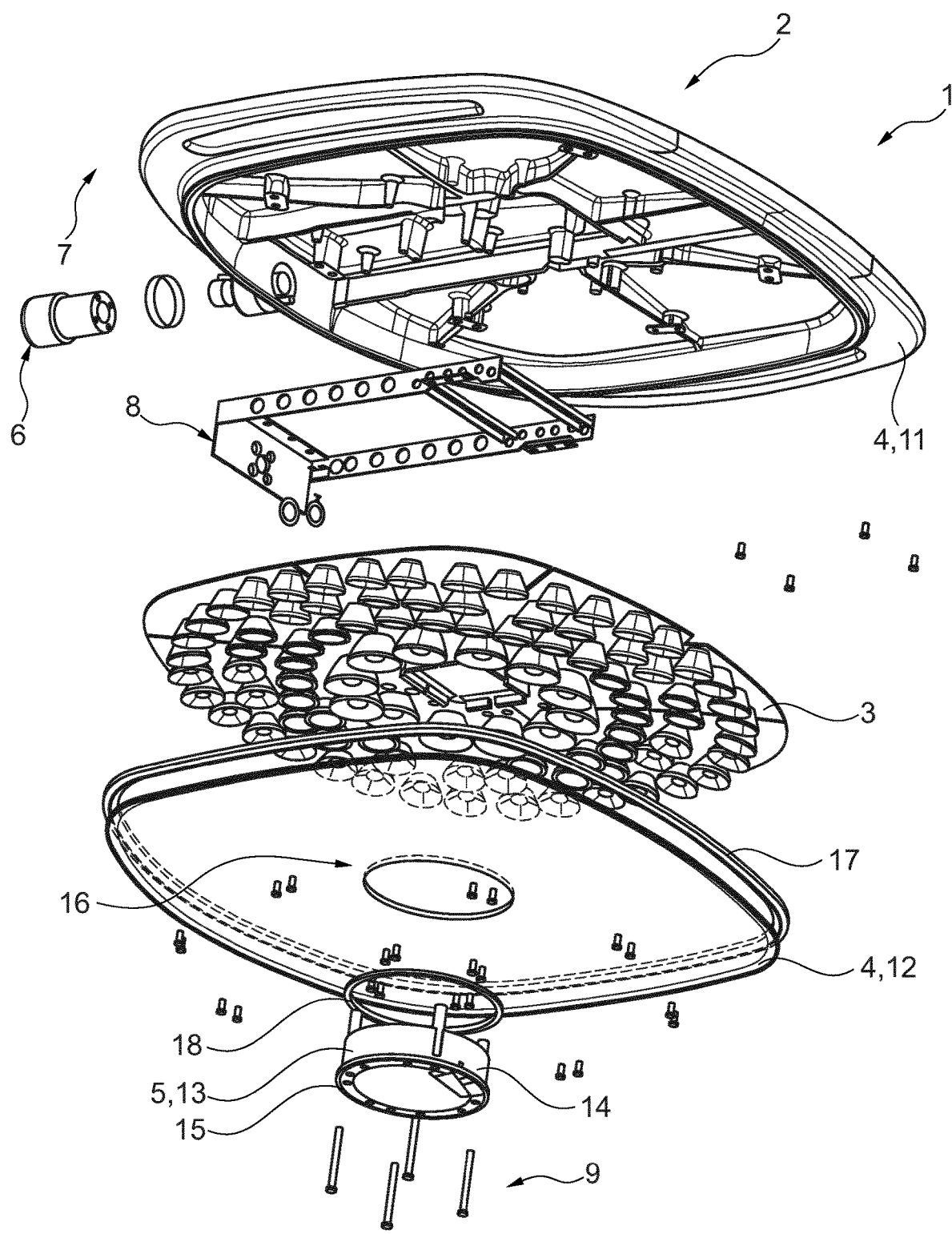
FIG. 1 shows a first exploded view of an operating lamp according to the invention comprising a lamp housing according to the invention.
Figure 2:
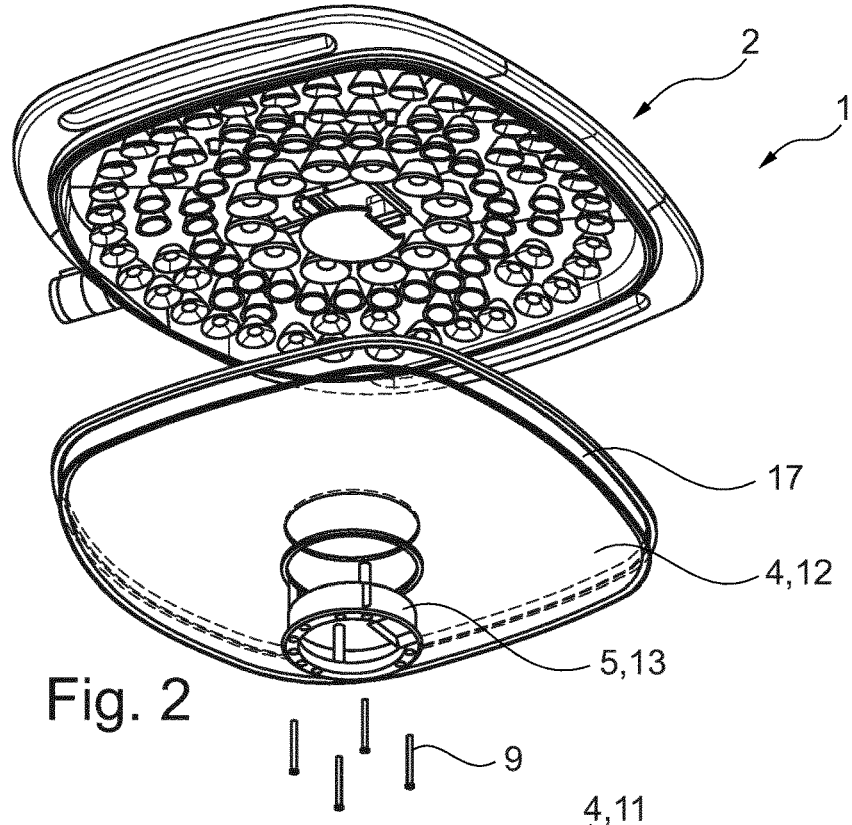
FIG. 2 shows a second exploded view of the operating lamp.
Figure 3:
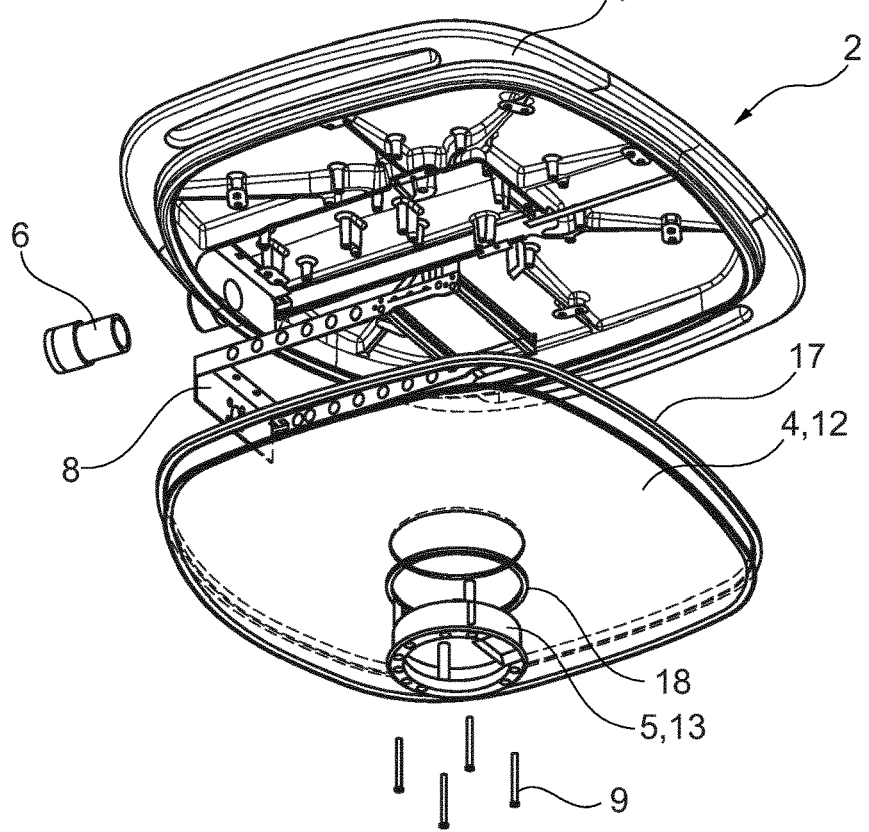
FIG. 3 shows an exploded view of the lamp housing.
Figure 4:
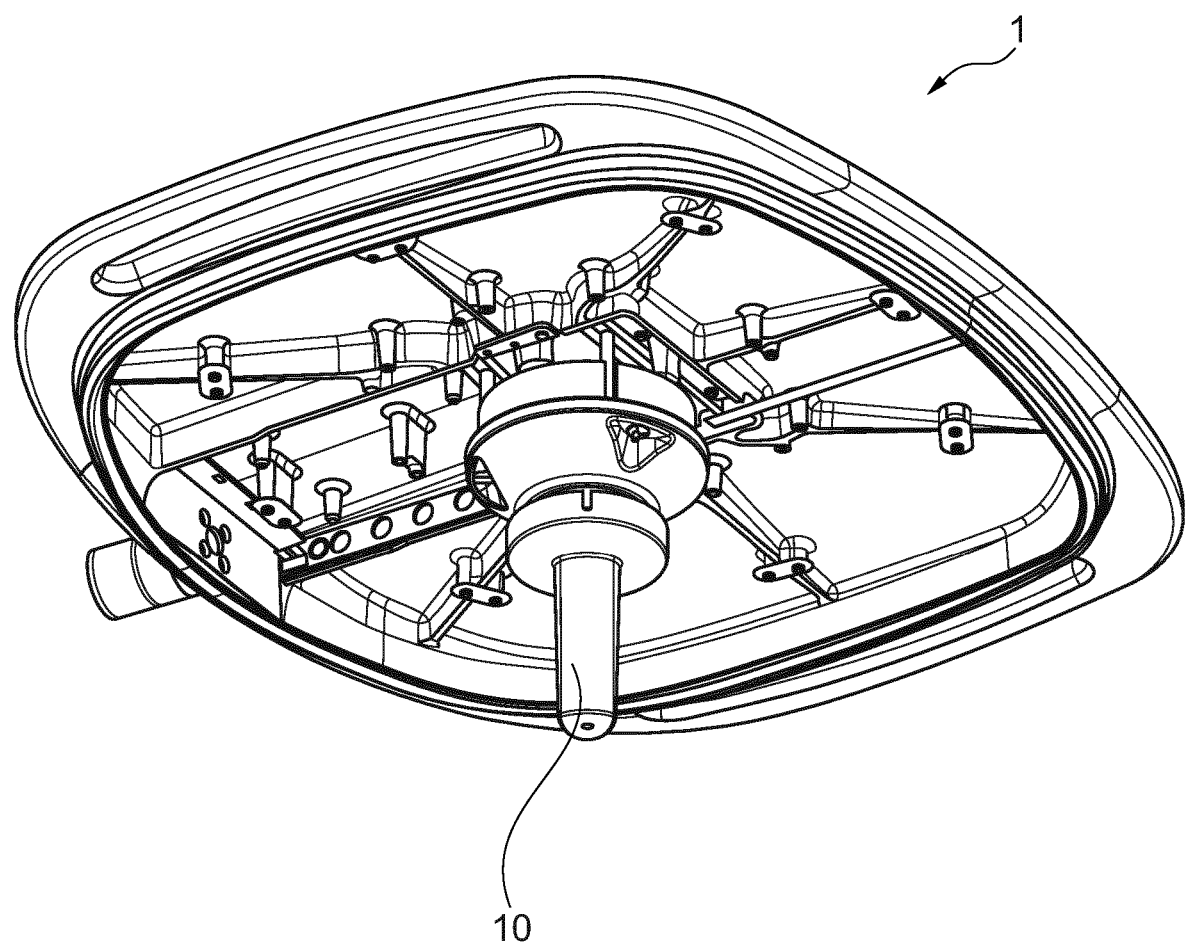
FIG. 4 shows a perspective view of the operating lamp with a gripping device arranged thereon.

FIGS. 1 to 4 illustrate a lamp housing 1 according to the invention of an operating lamp 2. In the lamp housing 1 at least one illuminant 3 can be installed to be sealed against the environment in a dust-tight manner. The illuminant 3 is formed by a lamp panel in the shown embodiments.

The lamp housing 1 has a housing body 4, a closure element 5 closing the housing body 4 and a bearing device 6 for fastening the lamp housing 1 to a supporting device 7. The supporting device 7 is usually formed by a supporting arm on which the operating lamp 2 is arranged. The supporting device 7 is not explicitly shown in the drawings.

In accordance with the invention, the lamp housing 1 includes a support 8 by means of which a force introduced via the closure element 5, especially for displacing the operating lamp 2, and/or a weight force of the lamp housing 1 can be transferred to the bearing device 6. The support 8 is formed separately from the housing body 4. The support 8 forms a supporting structure for the operating lamp 2. The support 8 and the housing body 4 are made from different materials. In the illustrated embodiments, the support 8 is formed by a steel cross-beam. The support 8 is a sheet metal part forming a frame structure. The support 8 is disposed inside the lamp housing 1.

The support 8 is directly connected, through the housing body 4, to the bearing device 6. The bearing device 6 is a one-sided lateral bearing. The closure element 5 is fastened to the support 8 via a connection element 9. In the shown embodiment, the connection element 9 is formed by a plurality of screws, in this case four screws. The screws are screwed in a direction along the optical path of the illuminant 3. The closure element is thus fastened to the support 8 directly via the connection element 9. Hence, the force is transmitted directly, viz. rather than via the housing body 4, to the support 8. The housing body 4 is also fastened to the support 8. The housing body 4 substantially does not transfer any forces which occur by the movement of the operating lamp 2 and/or the weight of the operating lamp 2.

The connection element 9 is outwardly covered. This means that there are no external screws. In the shown embodiment (cf. FIG. 4) the lamp housing 1 includes a gripping device 10 fastened to the closure element 5 while covering the connection element 9. The gripping device 10 is in the form of a handle. The gripping device 10 is arranged centrally on an outer face of the lamp housing and, resp., the housing body 4. The gripping device 10 can be replaced. In the shown embodiment, the gripping device 10 is arranged on the closure element 5 by means of one or more screws, tommy screws in this case. Alternatively, or additionally, for covering the connection element 9, the lamp housing 1 may include a covering device which is fastened to the closure element 5 while covering the connection element 9.

The housing body 4 has a multi-part structure. The housing body 4 includes an upper part 11 and a lower part 12 formed separately from the upper part 11. The lower part 12 is connected to the upper part 11. The lower part 12 is in the form of a closure glass. The lower part 12 is formed to be light-transparent at least in the region of an optical path produced by the illuminant 3. The lower part 12 is fastened to the upper part 11 by the closure element 12. The closure element 5 prestresses the lower part 12 against the upper part 11. In this way, the lower part 12 is pressed against the upper part 11 so that a tight connection is formed. Preferably, the upper part 11 is made from polyurethane. The lower part 12 is preferably made from tempered glass such as from mineral glass.

The closure element 5 is in the form of a holding ring 13. The closure element 5 is arranged centrally on the lamp housing 1. The closure element 5 includes an annular portion 14 and a flange portion 15. The annular portion passes through a recess 16 of the lower part 12. The flange portion 15 projects radially outwardly from the annular portion 14. In the mounted state, an end facing away from the flange portion 15 abuts on the upper part 11. The flange portion 15 abuts on an outer face of the lower part 12. In this way, the flange portion 15 presses the lower part 12 against the upper part. The connection element 9 passes through the closure element 5 radially inside the flange portion 15.

The lamp housing 1 includes a housing body seal 17 for sealing an interior of the lamp housing 1. The housing body seal 17 is interposed between the upper part 11 and the lower part 12. For sealing an interior of the lamp housing 1, the lamp housing 1 includes a closure seal 18. The closure seal 18 is interposed between the lower part 12 and the closure element 5. In particular, the closure seal 18 is interposed between the flange portion 15 and an outer face of the lower part 12. Preferably, the closure seal 18 is connected radially outside of the recess 16 while enclosing said recess 16.

The invention claimed is:

1. A lamp housing for an operating lamp in which lamp housing is adapted for the installation of at least one illuminant, said lamp housing comprising a housing body with a shell-shaped upper part and a shell-shaped lower part being formed separate from the upper part, a closure element which closes the housing body by fastening the lower part to the upper part, and a bearing device for fastening the lamp housing to a supporting device, characterized in that the lamp housing has a support formed separately from the housing body which support is completely arranged inside the lamp housing and which support is in the form of a cross-beam forming a closed frame structure and by means of which a force introduced via the closure element or a weight force of the lamp housing is transferred to the bearing device.

2. The lamp housing according to claim 1, wherein the closure element is fastened to the support via a connection element.

3. The lamp housing according to claim 2, wherein the lamp housing includes a gripping device or a covering device, wherein the gripping device or the covering device is adapted to be fastened to the closure element while covering the connection element.

4. The lamp housing according to claim 1, wherein the lower part being light-transparent at least in the region of an optical path produced by the illuminant.

5. The lamp housing according to claim 4, wherein the closure element fastens the lower part to the upper part.

6. The lamp housing according to claim 4, wherein the support is made from steel or the upper part is made from polyurethane or the lower part is made from tempered glass.

7. The lamp housing according to claim 1, wherein the closure element is in the form of a holding ring which is disposed centrally on the lamp housing.

8. The lamp housing according to claim 1, wherein the closure element includes an annular portion which passes through a recess of the lower part and a flange portion radially outwardly projecting from the annular portion which flange portion abuts on an outer face of the lower part.

9. The lamp housing according to claim 1, wherein for sealing an interior of the lamp housing, the lamp housing includes a housing body seal interposed between the upper part and the lower part or a closure seal interposed between the lower part and the closure element.

10. The lamp housing according to claim 1, wherein the support forms a frame structure.

11. The lamp housing according to claim 1, wherein the support and the housing body are made from different materials, wherein the material of the support has a higher strength or rigidity than the material of the housing body.

12. The lamp housing according to claim 1, wherein the closed frame structure is formed by longitudinal struts and cross struts.

13. The lamp housing according to claim 1, wherein the closed frame structure extends inside the housing body from the supporting device to beyond a center of the lamp housing or beyond the closure element.

14. A lamp housing for an operating lamp in which lamp housing is adapted for the installation of at least one illuminant, said lamp housing comprising a housing body, a closure element which closes the housing body, and a bearing device for fastening the lamp housing to a supporting device, characterized in that the lamp housing has a support formed separately from the housing body which support is in the form of a cross-beam forming a closed frame structure and by means of which a force introduced via the closure element or a weight force of the lamp housing is transferred to the bearing device, wherein the closed frame structure comprises an inner strut forming, together with a part of the frame structure, an inner closed frame structure surrounding the closure element.

\* \* \* \* \*